US008642080B2

(12) United States Patent
Bender et al.

(10) Patent No.: US 8,642,080 B2
(45) Date of Patent: Feb. 4, 2014

(54) DRUG DELIVERY SYSTEM COMPRISING POLYOXAZOLINE AND A BIOACTIVE AGENT

(75) Inventors: Johannes Caspar Mathias Elizabeth Bender, Utrecht (NL); Richard Hoogenboom, Terneuzen (NL); Patrick Andreas Anton van Vliet, Voorschoten (NL)

(73) Assignee: Bender Analytical Holdong B.V., Utrecht (NL)

( * ) Notice: Subject to any disclaimer, the term of this patent is extended or adjusted under 35 U.S.C. 154(b) by 0 days.

(21) Appl. No.: 13/381,271

(22) PCT Filed: Jun. 28, 2010

(86) PCT No.: PCT/NL2010/050403
§ 371 (c)(1),
(2), (4) Date: Mar. 30, 2012

(87) PCT Pub. No.: WO2011/002285
PCT Pub. Date: Jan. 6, 2011

(65) Prior Publication Data
US 2012/0183606 A1    Jul. 19, 2012

(30) Foreign Application Priority Data
Jun. 29, 2009   (EP) .................................... 09164023

(51) Int. Cl.
*A61K 9/20*   (2006.01)
*A61K 9/48*   (2006.01)
*A61K 9/14*   (2006.01)
*A01N 43/16*  (2006.01)

(52) U.S. Cl.
USPC ........... 424/464; 424/489; 424/451; 424/484; 514/454

(58) Field of Classification Search
None
See application file for complete search history.

(56) References Cited

U.S. PATENT DOCUMENTS

| 4,990,339 | A | 2/1991 | Scholl et al. |
| 5,536,505 | A | 7/1996 | Wilson et al. |
| 6,716,450 | B1 | 4/2004 | Yin et al. |
| 2007/0183987 | A1 | 8/2007 | Jensen |
| 2008/0026040 | A1* | 1/2008 | Farr et al. ...................... 424/443 |

FOREIGN PATENT DOCUMENTS

CA    2253700    6/1999

OTHER PUBLICATIONS

Ghaste, et al., "Solid Dispersions: An Overview," Pharmaceutical Reviews, [on line], vol. 7, No. 5, Feb. 11, 2009, (12 pages), XP009137552, Retrieved from the Internet: URL: http://www.pharmainfo.net/reviews/solid-dispersions-overview> [retrieved on Feb. 11, 2009].
Shenouda, et al., "A controlled release delivery system using two hydrophilic polymers," International Journal of Pharmaceutics, (1990) vol. 61, pp. 127-134, XP023724640.
Thakkar, et al., "Solid dispersion approach for overcoming bioavailability problems due to polymorphism of nabilone, a cannabinoid derivative," Communications, J. Pharm. Pharmac., (1977), vol. 29, pp. 783-784.
Tiwari, et al., "Solid Dispersions: An Overview to Modify Bioavailability of Poorly Water Soluble Drugs," International Journal of PharmaTech Research, vol. 1, No. 4, pp. 1338-1349, Oct.-Dec. 2009, CODEN (USA): IJPRIF, ISSN: 0974-4304, XP009137553.
Search Report in International Application No. PCT/NL2010/050403 mailed Aug. 26, 2010.

* cited by examiner

*Primary Examiner* — Kyle Purdy
(74) *Attorney, Agent, or Firm* — Gilberto M. Villacorta; Sunit Talapatra; Foley & Lardner LLP

(57) ABSTRACT

The invention relates to drug delivery systems comprising a water-soluble polymer matrix and a bioactive agent entrained therein, said water soluble polymer matrix containing at least 50 wt. % of polyoxazoline having a molar mass of at least 5 40,000 g/mol. The drug delivery systems of the present invention offer the advantage that the bioactive agent is readily released when the drug delivery system is contacted with water. The drug delivery system can be in the form of a solid dispersion, a mucoadhesive sheet, a tablet, a powder, a capsule.

16 Claims, No Drawings

DRUG DELIVERY SYSTEM COMPRISING POLYOXAZOLINE AND A BIOACTIVE AGENT

TECHNICAL FIELD OF THE INVENTION

The present invention relates to a drug delivery system for the controlled release of bioactive agents. More particularly, the present invention relates to a drug delivery system comprising a polyoxazoline-based water-soluble polymer matrix and a bioactive agent that is entrapped within said polymer matrix, e.g. in the form of solid dispersion. Examples of drug delivery systems according to the present invention include oral delivery systems and trans-mucosal delivery systems. These delivery systems can, for example, take the shape of a powder, a tablet, a capsule or a mucoadhesive sheet.

The invention also provides methods for the preparation of the drug delivery systems described herein.

BACKGROUND OF THE INVENTION

Controlled drug delivery occurs when a polymer, whether natural or synthetic, is judiciously combined with a bioactive agent in such a way that the bioactive agent is released from the material in a predesigned manner. The release of the bioactive agent may be constant over a long period, it may be cyclic over a long period, or it may be triggered by the environment or other external events.

Providing control over drug delivery can be very important at times when traditional oral or injectable drug formulations cannot be used. These include situations requiring the slow release of water-soluble drugs, the fast release of hydrophobic drugs, drug delivery to specific sites, drug delivery using nanoparticulate systems, delivery of two or more agents with the same formulation, and systems based on carriers that can dissolve or degrade and be readily eliminated. The ideal drug delivery system should be inert, biocompatible, mechanically strong, comfortable for the patient, capable of achieving high drug loading, safe from accidental release, simple to administer and remove, and easy to fabricate and sterilize.

To be successfully used in controlled drug delivery formulations, a polymeric material must be chemically inert and free of leachable impurities. It must also have an appropriate physical structure, with minimal undesired aging, and be readily processable. Some of the polymers that are currently being used or studied for controlled drug delivery include: poly(2-hydroxy ethyl methacrylate); poly(N-vinyl pyrrolidone); poly(methyl methacrylate); poly(vinyl alcohol; poly (acrylic acid); polyacrylamide; poly(hydroxypropyl-methacrylamide) poly(ethylene-co-vinyl acetate); poly (ethylene glycol); poly(methacrylic acid).

However, in recent years additional polymers designed primarily for medical applications have entered the arena of controlled release. Many of these materials are designed to degrade within the body, among them: polylactides (PLA); Polyglycolides (PGA); poly(lactide-co-glycolides) (PLGA); polyanhydrides; polyorthoesters.

Up to 40% of lipophilic drug candidates fail to reach the market although exhibiting interesting pharmacodynamic activities. Various formulation strategies have been investigated to improve the solubility and the rate of dissolution and hence the oral bioavailability of lipophilic drugs. These strategies include solubilization, addition of surfactants, use of different polymorphic/amorphic drug forms, reduction of drug particle size and complexation.

Non-traditional technologies for improving the solubility and dissolution of lipohilic drugs, including drug-polymer solid solutions and solid dispersions, have gained increasing attention. The pharmaceutical application of solid solutions/dispersions to enhance oral bioavailability was first envisioned in 1961. Since then, only five commercial products have been launched that use the solid solution/dispersion approach.

Different water-soluble polymeric excipients have been employed as carriers of solid solutions/dispersions. Among them, polyethylene glycols (PEG, Mw 1500-20,000) are most commonly used due to their good solubility in water and in many organic solvents, low melting points (under 65° C.), ability to solubilize some compounds and improvement of compound wettability. Other polymeric carriers that have been suggested as carriers in solid solutions/dispersions include polyvinyl pyrrolidone (PVP), polyvinylalcohol (PVA), polyvinyl-pyrrolidone polyvinylacetate copolymer (PVP-PVA), hydroxypropyl methylcellulose (HPMC), hydroxypropyl cellulose (HPC), polyurethanes, Poloxamer 407 and polyvinyl caprolactam-polyvinyl acetate-polyethylene glycol graft copolymer (Soluplus®, BASF).

The use of poly(2-oxazoline)s in drug delivery systems and dental formulations is known from the prior art.

WO 2009/156180, which was published after the priority date of the present application, describes a composition, comprising:
(a) at least one copolymer comprising repeating units of formula (I) $(CH_2)_2NCOR^A$ with $R^A$ being selected such that the repeating unit of formula (I) is hydrophilic; and repeating units of the formula (II) $(CH_2)_2NCOR^B$ with $R^B$ being selected such that the repeating unit of formula (II) is more hydrophobic than the repeating unit of formula (I); and
(b) one or more active agent(s).

WO 02/26179 describes a pain relief composition as an implantable pellet form and a method to relieve pain using such implantable pellets in which formulations comprise one or more anesthetic agents in combination with one or more analgesic agents and excipients like polyethylene glycol, starch, dextran, polyvinylalcohol, poly(2-ethyl-2-oxazoline) and mixtures thereof. The pellets are not intended for oral application. There is no referral to the preparation of solid solutions nor solid amorphous suspensions including the API.

U.S. Pat. No. 6,730,321 describes a drug delivery system suitable for oral administration that facilitates a pulsatile release of the active agent. Poly(2-oxazoline) is mentioned as a possible co-excipient to be used in the formulation.

U.S. Pat. No. 5,536,505 describes a controlled release matrix system comprising a homogenous mixture of poly(2-ethyl-2-oxazoline) and cellulose acetate, and of a water-soluble active ingredient, wherein said cellulose acetate is present in the amount of 95 to 20 weight % and the poly(2-ethyl-2-oxazoline) is present in the amount of 5 to 80 weight %, based on the total weight percentages of the poly(2-ethyl-2-oxazoline) and cellulose acetate equaling 100 weight %, and wherein said active ingredient is present in the amount of 0.01 to 40 weight % based on the total weight percentages of poly(2-ethyl-2-oxazoline), cellulose acetate and active ingredient equaling 100 weight %. It is stated that, poly(2-ethyl-2-oxazoline) is compatible with the cellulose acetate of the invention in that it is capable of yielding a clear film and one glass transition temperature by either differential scanning calorimetry or dynamic mechanical thermal analysis.

U.S. Pat. No. 4,990,339 describes an aqueous soluble dermal treatment film which comprises: (a) a structural layer comprising a poly(2-alkyl-2-oxazoline) polymer; and (b) a pressure sensitive adhesive layer comprising 10-75 wt. % of a poly(2-alkyl-2-oxazoline) polymer, 10-75 wt. % of a functional diluent comprising a hydroxy compound or a carboxylic acid compound; and 5-35 wt. % of a compatible tackifier US 2007/0183987 describes a dental whitening composition and a bleaching gel comprising poly(2-ethyl-2-oxazoline) and a peroxide.

SUMMARY OF THE INVENTION

The inventors have designed drug delivery systems that readily release the bioactive agent contained therein when brought into contact with water, even if these bioactive agents are highly lipophilic and virtually water insoluble. The drug delivery systems of the present invention further offer the advantage that they protect the bioactive agent contained therein against degradation, notably against degradation that is induced by oxygen.

The drug delivery systems of the present invention comprise a water-soluble polymer matrix and a bioactive agent entrained therein, said water soluble polymer matrix containing at least 50 wt. % of polyoxazoline having a molar mass of at least 40,000 g/mol.

Poly2-oxazoline) is a synthetic polymer that swells when brought into contact with water and that dissolves completely, provided sufficient free water is available. The fact that polyoxazoline dissolves in non-aqueous as well as aqueous environment sets it apart from most synthetic polymers that are used in drug delivery systems for controlled release.

The use of polyoxazoline in the drug delivery systems of the present invention offers the following advantages:
- due to its water solubility, polyoxazoline readily releases the bioactive agent that is entrapped in the polyoxazoline-based polymer matrix;
- polyoxazoline polymers are easy to process as they readily dissolve in organic solvents, such as ethanol. Thus, polyoxazoline, bioactive agent and other excipients, like plasticizers, can be dissolved in an organic solvent to, for instance, produce thin films by solvent casting;
- Polyoxazoline is capable of effectively preventing (re)crystallization of amorphous bioactive agent due to its amphiphilic nature and solubilization capacity;
- the polyoxazoline polymer matrix very effectively protects bioactive agents against e.g. oxidation and hydrolysis;
- Polyoxazoline is aprotic and chemically inert (unlike, for instance, Eudragit E that degrades cefuroxime axetil as the dimethylamino group of Eudragit E interacts with Cefuroxime axetil resulting in carboxylate salt formation).
- the polyoxazoline polymer matrix has strong muco-adhesive properties.

The inventors have unexpectedly discovered that polyoxazolines having a molecular weight of at least 40,000 g/mol are extremely stable, even when exposed to gastric conditions for a prolonged period of time. Thus, oral use of polyoxazoline and the resulting exposure to gastric fluid is not accompanied by hydrolysis of the polyoxazoline polymer, resulting in the formation of unwanted, potentially absorbable polymer fragments. Hence these high molecular weight polyoxazolines are perfectly suited for oral administration as no potentially harmful degradation products are formed when the polymer is transported through the gastrointestinal tract. High molecular weight polyoxazoline additionally offer the advantage that it renders strong amorphous films that can be (cryogenically) milled into small particles suitable for tablet formulation.

One aspect of the present invention relates to drug delivery system comprising a water-soluble polymer matrix; and a bioactive agent that is entrapped within the polymer matrix in the form of a solid dispersion of amorphous bioactive agent in the water-soluble polymer matrix, said water-soluble polymer matrix containing at least 50 wt. % of polyoxazoline having a molar mass of at least 40,000 g/mol and said amorphous bioactive agent being contained in the solid dispersion in a concentration of at least 0.5% by weight of the water-soluble polymer matrix.

The inventors have found that polyoxazoline, notably poly (2-oxazoline), can advantageously be used to prepare solid dispersions in which a bioactive agents is entrapped in a stabilized amorphous state. It is generally recognized that in order to render, for instance, lipophilic bioactive agents bioavailable it is advantageous to employ these bioactive agents in an amorphous state. However, since the amorphous state is metastable it is often very difficult, if not impossible, to prevent premature conversion of the high energy amorphous polymorph into a low energy crystal form. The solid dispersions of the present invention provide a remedy for this problem.

The solid dispersions employed in the present drug delivery system can be prepared without difficulty. Because polyoxazoline is not only soluble in water, but also in a wide range of organic solvents, polyoxazoline-based solid dispersions can suitably be produced by dissolving the bioactive agent and the polyoxazoline in a common solvent, followed by removal of the solvent by means of, for instance, evaporation under vacuum, freeze drying or spray drying. Polyoxazoline solid dispersions may also be produced by combining the bioactive agent and the polyoxazoline to form a mixture having a temperature above the glass transition temperature of said mixture and by cooling the mixture to a temperature below said glass transition temperature at a sufficiently high rate.

Another aspect of the invention relates to a drug delivery system in the form of a powder having a mass weighted average diameter of 0.1-250 µm, said drug delivery system comprising 40-99.999 wt. % of a water-soluble polymer matrix; and 0.001-95% by weight of the water-soluble polymer matrix of a delivery vehicle that is entrapped within said polymer matrix and that comprises 0.001-100 wt. % of a bioactive agent; wherein the water-soluble polymer matrix contains at least 30 wt. %, preferably at least 50 wt. % of polyoxazoline having a molar mass of at least 40,000 g/mol, and wherein the bioactive agent is not a peroxide.

Yet another aspect of the present invention relates to a drug delivery system in the form of a muco-adhesive sheet comprising at least 20 wt. % of a water-soluble polymer matrix in the form of thin film; a water-insoluble backing membrane; and 0.001-95% by weight of the water-soluble polymer matrix of a delivery vehicle that is entrapped within the polymer matrix and that comprises at least 0.001 wt. % of a water-insoluble bioactive agent and at least 50 wt. % of a pharmaceutically acceptable solvent selected from the group of polyols, esters of polyols and short chain carboxylic acids and combinations thereof; wherein the water-soluble polymer matrix contains at least 30 wt. % of polyoxazoline having a molar mass of at least 40,000 g/mol, and wherein the bioactive agent is not a peroxide.

The present invention also provides methods for the preparation of drug delivery systems as defined herein. One method comprises combining a solvent, the polyoxazoline and the bioactive agent to produce a solution of the polyoxazoline in the solvent, followed by removal of the solvent. The other method comprises combining the bioactive agent and the polyoxazoline to form a mixture having a temperature above the glass transition temperature of said mixture, followed by cooling the mixture to a temperature below said glass transition temperature at a sufficiently high rate to solidify the polyoxazoline and the bioactive agent in an amorphous state.

DETAILED DESCRIPTION OF THE INVENTION

A first aspect of the present invention relates to a drug delivery system comprising a solid dispersion of an amorphous bioactive agent in a water-soluble polymer matrix, said water-soluble polymer matrix containing at least 50 wt. % of polyoxazoline having a molar mass of at least 40,000 g/mol and said amorphous bioactive agent being contained in the solid dispersion in a concentration of at least 0.5% by weight of the water-soluble polymer matrix.

The term "solid dispersion" as used herein refers to a system in a solid state (as opposed to a liquid or gaseous state) comprising at least two components, wherein at least one component (including the bioactive agent) is dispersed evenly throughout one or more other components (including the water-soluble polymer matrix). When the said dispersion is chemically and physically homogenous throughout and consists of one phase as defined in thermodynamics, such a solid dispersion is referred to herein as a "solid solution".

Besides solid solutions the term "solid dispersion" also encompasses dispersions that are not chemically and physically uniform throughout and that comprise a dispersed solid phase (including the bioactive agent) that is homogeneously distributed throughout a continuous solid phase of different chemical composition (including the water-soluble polymer matrix) in the form of extremely small particles having a volume weighted mean diameter of less than 100 nm.

The term "amorphous" as used herein in relation to solid materials refers to a material that is a solid and in which there is no long-range order of the positions of the molecules. This lack of order distinguishes amorphous solids from crystalline solids.

The term "polyoxazoline" as used herein refers to a poly (N-acylalkylenimine).

The water-soluble polymer matrix of the present drug delivery system can be amorphous, crystalline or it can comprise both amorphous and crystalline elements. According to a particularly preferred embodiment, the water-soluble polymer matrix is in an amorphous state.

According to a particularly preferred embodiment, the solid dispersion comprised in the present drug delivery system is a solid solution. Solid solutions are preferred because the bioactive agent contained therein is usually readily bioavailable to the organisms to which they are administered. This advantage can probably be explained by the ease with which said solid solutions can form liquid solutions when contacted with a liquid medium such as gastric juice. The ease of dissolution may be attributed at least in part to the fact that the energy required for dissolution of the components from a solid solution is less than that required for the dissolution of components from a crystalline or microcrystalline solid phase.

In order to ensure that a solid solution is sufficiently stable, it is advisable to ensure that the $T_g$ of the solid solution is at least 40° C. higher than the envisaged storage temperature. Accordingly, it is preferred that the present drug delivery system in the form of a solid solution has a $T_g$ of at least 45° C., more preferably of at least 55° C. and most preferably of at least 60° C.

Poly(2-ethyl-2-oxazoline) has a glass transition temperature ($T_g$) of about 70° C. Due to this relatively high $T_g$, poly(2-ethyl-2-oxazoline) can be combined with bioactive agents having a much lower $T_g$ to produce solid solutions having a $T_g$ that lies between the $T_g$ of poly(2-ethyl-2-oxazoline) and that of the bioactive agent, the exact $T_g$ being dependent on the ratio of bioactive agent to poly(2-ethyl-oxazoline). The same holds for related poly(2-oxazoline)s. The benefits of this approach are particularly appreciated in case the bioactive agent has a $T_g$ of not more than 50° C. More preferably, the bioactive agent has a $T_g$ of less 40° C., even more preferably of less than 30° C. and most preferably of less than 20° C. Typically, the $T_g$ of the bioactive agent is at least −30° C., preferably at least −15° C.

Examples of bioactive agents having a relatively low $T_g$ that may suitably be employed in the present drug delivery system include propofol, benzyl benzoate, fomepizole, carmustine, pilocarpine, ephedrine, permethrin, phenoxybenzamine, menthol, trimipramine, trimethadione, diethylcarbamazine, isoflurane, guanidine, paracetamol, diazepam, alprazolam, nifedipine, felodipine, tetrahydrocannabinol, cannabidiol, cannabigerol, tetrahydrocannabivarin (tetrahydrocannabivarol), cannabichromene, vitamins (e.g. retinol, thiamine, ergocalciferol, cholecalciferol, tocoferol), amino acids (e.g., L-arginine, L-lysine, L-histidine) and combinations thereof.

In addition, active pharmaceutical ingredients that transform into a glassy state with a relatively low $T_g$, after melting, cooling and subsequent reheating, are also applicable. Examples include itraconazole and other well known amorphous drugs with a (relatively) low molecular weight like quinapril hydrochloride (Accupril®), zafirlukast (Accolate®), nelfinavir mesylate (Viracept®), lopinavir (Kaletra®, Aluvia®), rosuvastatin (Crestor®) and the antibiotic Zinnat®/Ceftin® (cefuroxime axetil).

According to a particularly preferred embodiment, the present drug delivery system is a solid solution of the bioactive agent in the water-soluble polymer matrix, said bioactive agent having a $T_g$ of −30° C. to 30° C. and being contained in the drug delivery device in a concentration of 0.5-30%, more preferably 0.5-20% and most preferably 0.5-10% by weight of the water-soluble polymer matrix. The presence of significant amounts of crystalline or microcrystalline material in the drug delivery device can be demonstrated by, for instance, thermal analysis (DSC) or X-ray diffraction analysis (XRD). Typically, in the present drug delivery system, at least 98% by weight of the total amount of bioactive agent is present in an amorphous state. Likewise, preferably at least 98% by weight of the total amount of the water-soluble polymer matrix is in an amorphous state.

In another embodiment of the drug delivery system the solid dispersion contains the amorphous bioactive agent in the form of nanoparticles having a volume weighted average diameter of less than 80 nm, preferably of less than 50 nm. The extremely small size of these nanoparticles favors the quick dissolution of the bioactive agent.

The use of a solid dispersion in accordance with the present invention offers the advantage that it enables the preparation of drug delivery systems having a very high load of bioactive agent. Preferably, the amorphous bioactive agent is contained in the solid dispersion in a concentration of at least 5% by weight of the water-soluble polymer matrix. Even more preferably, the bioactive agent is contained in the solid dispersion in a concentration of 10-150% by weight of the water-soluble polymer matrix. Most preferably, the bioactive agent is contained in the solid dispersion in a concentration of 15-120% by weight of the water-soluble polymer matrix.

The drug delivery systems according to the present invention are particularly suited for oral and transmucosal administration. Thus, in accordance with a preferred embodiment, the drug delivery system is selected from a powder, a tablet, a capsule and a mucoadhesive sheet.

Typically, the drug delivery system comprises 5-100 wt. %, preferably 10-100 wt. % and most preferably 15-90 wt. % of the solid dispersion.

According to a particularly preferred embodiment, the drug delivery system is a powder. Advantageously, said powder has a mass weighted average diameter of 0.1-250 μm. The drug delivery system in the form of a powder can be used in oral formulations, e.g. tablets, capsules and aqueous (reconstituted) preparations.

In accordance with another advantageous embodiment the drug delivery system is a mucoadhesive sheet, said mucoadhesive sheet typically comprising at least 20 wt. % of the water-soluble polymer matrix, e.g. in the form of a thin film. The mucoadhesive sheet may suitably contain a backing membrane that is not water-soluble. The use of a water-insoluble backing membrane ensures that the bioactive agent is predominantly released in the direction of the mucosa and may also impart rigidity to the mucoadhesive sheet. The water-insoluble backing membrane may suitably be made of ethyl cellulose.

The water-soluble polymer matrix typically represents 20-99.999 wt. % of the present drug delivery system. The water-soluble polymer matrix may represent only a minor fraction of the drug delivery system, e.g. in case the drug delivery system contains further elements, such as a backing membrane in case the drug delivery system is a muco-adhesive sheet or a liquid filling in case the drug delivery system is a liquid capsule.

Another aspect of the invention relates to a drug delivery system in the form of a powder having a mass weighted average diameter of 0.1-250 μm, said drug delivery system comprising 40-99.999 wt. % of a water-soluble polymer matrix; and 0.001-95% by weight of the water-soluble polymer matrix of a delivery vehicle that is entrapped within the polymer matrix and that comprises 0.001-100 wt. % of a bioactive agent; wherein the water-soluble polymer matrix contains at least 30 wt. %, preferably at least 50 wt. % of polyoxazoline having a molar mass of at least 40,000 g/mol, and wherein the bioactive agent is not a peroxide.

The term "delivery vehicle" as used herein refers to a discrete volume of material within the polymer matrix that contains or consists of bioactive agent. In accordance with a preferred embodiment, the delivery vehicle is homogenously distributed throughout the water-soluble polymer matrix.

According to a preferred embodiment of the invention the delivery vehicle contains at least 50 wt. %, preferably at least 70 wt. % of a pharmaceutically acceptable solvent and the bioactive agent is dissolved in said pharmaceutically acceptable solvent. According to yet another preferred embodiment the delivery vehicle contains at least 50 wt. %, preferably at least 70 wt. % of pharmaceutically acceptable water-soluble excipient other than polyoxazoline, and the bioactive agent is entrapped in said excipient.

In accordance with another advantageous embodiment, the delivery vehicle contained in the powdery drug delivery system contains 0.001-100 wt. %, more preferably 0.1-100 wt. % and most preferably 1-100 wt. % of the bioactive agent.

In accordance with a highly preferred embodiment, the present drug delivery system is a free flowing powder having a mass weighted average diameter of 0.5-220 μm, more preferably of 1-200 μm, and most preferably of preferably of 10-100 μm, said powder comprising at least 40 wt. % of the water-soluble polymer matrix. This powder may suitably be used in the manufacture of e.g. oral dosage units or in the preparation of formulations for local administration, e.g. creams or gels.

Accordingly, the present invention further provides an oral dosage unit selected from a tablet and a capsule, said oral dosage unit comprising a drug delivery system in the form of a powder as described herein before. In case the powdery drug delivery system is employed in an oral dosage unit, it is suitably combined with other pharmaceutically acceptable materials such as excipient, binders, disintegrants, coatings and flavors. Advantageously, the oral dosage unit comprises 10-80 wt. % of the powdery drug delivery system, 20-90 wt. % of excipient and 0-20 wt. % of other pharmaceutically acceptable components.

Typically, the oral dosage units according to the present invention have a weight of 5-2500 mg. The powdery drug delivery system according to the present invention preferably represents at least 5 wt. % of the oral dosage unit. More preferably, said drug delivery system constitutes 10-90%, even more preferably 15-75% by weight of the oral dosage unit.

The oral dosage unit of the present invention is suitably coated with an enteric coating. The application of an enteric coating effectively prevents the degradation of the polyoxazoline under gastric conditions and further delays the release of the bioactive agent until the dosage unit has reached the intestines.

Yet another aspect of the present invention relates to a drug delivery system in the form of a muco-adhesive sheet comprising at least 20 wt. % of a water-soluble polymer matrix in the form of thin film; a water-insoluble backing membrane; and 0.001-95% by weight of the water-soluble polymer matrix of a delivery vehicle that is entrapped within the polymer matrix and that comprises at least 0.001 wt. % of a water-insoluble bioactive agent and at least 50 wt. % of a pharmaceutically acceptable solvent selected from the group of polyols, esters of polyols and short chain carboxylic acids and combinations thereof; wherein the water-soluble polymer matrix contains at least 30 wt. % of polyoxazoline having a molar mass of at least 40,000 g/mol, and wherein the bioactive agent is not a peroxide.

The use of a water-insoluble backing membrane ensures that the bioactive agent is predominantly released in the direction of the mucosa and may also impart rigidity to the mucoadhesive sheet. The water-insoluble backing membrane may suitably be made of ethyl cellulose.

In accordance with a preferred embodiment, the drug delivery systems of the present invention that comprise a delivery vehicle contain said delivery vehicle in concentration of 0.05-90%, most preferably 0.5-80% by weight of the water-soluble polymer matrix.

The drug delivery systems of the present invention typically contain the bioactive agent in a concentration of 0.005-95%, more preferably of 0.01-90%, and most preferably of 0.1-80% by weight of the water-soluble polymer matrix.

The present delivery systems offer the unexpected advantage that if the polymer matrix contains little or no water, the bioactive agent is very effectively protected against e.g. oxidation and/or hydrolysis. Accordingly, in an advantageous embodiment, the polymer matrix contains less than 5 wt. % of water. Even more preferably, the water-soluble polymer matrix contains less than 1 wt. % of water, most preferably, it contains even less than 0.5 wt. % of water.

The water-soluble polymer matrix of the present drug delivery system preferably contains at least 70 wt. %, most preferably at least 80 wt. % of polyoxazoline. Besides polyoxazoline, the water-soluble polymer matrix may contain other water-soluble polymers such as water-soluble polysaccharides and water-soluble proteins.

Preferably, the polyoxazoline employed in accordance with the present invention is a polymer wherein the repeating units are represented by the following formula (I):

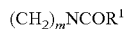

$R^1$ being selected from H, $C_{1-22}$ alkyl, cycloalkyl, aralkyl, aryl; and m being 2 or 3. The present invention also encompasses the use of polyoxazolines copolymers that comprise two or more different repeating units that are represented by formula (I).

Preferably, $R^1$ in formula (I) is selected from H and $C_{1-22}$ alkyl, even more preferably from H and $C_{1-4}$ alkyl. The integer m in formula (I) is preferably equal to 2. According to a preferred embodiment, the polyoxazoline employed in accordance with the present invention is a polymer, even more preferably a homopolymer of 2-alkyl-2-oxazoline, said 2-alkyl-2-oxazoline being selected from 2-methyl-2-oxazoline, 2-ethyl-2-oxazoline, 2-propyl-2-oxazoline, 2-butyl-2-oxazoline and combinations thereof. Most preferably, the polyoxazoline is a homopolymer of 2-ethyl-oxazoline.

As explained herein before, the inventors have discovered that high molecular weight polyoxazolines are particularly suitable for oral drug delivery as they are less susceptible to acid hydrolysis. Particularly favorable release properties can be realized with the present drug delivery system if a polyoxazoline having a molar mass of at least 60,000 g/mol, even more preferably of at least 150,000 g/mol and most preferably of at least 200,000 is employed. Typically, the polyoxazoline has a molar mass of less than 1,000,000 g/mol, more preferably of less than 600,000 g/mol.

The bioactive agent employed in the drug delivery system advantageously is selected from the group consisting of pharmaceutical drugs, vitamins and minerals. Even more preferably, the bioactive agent is selected from cardiovascular drugs, hypoglycemic drugs, sedatives/hypnotics; antiepileptics, psychopharmacologic agents, analgesics, antipyretics, anti-inflammatory agents, anti-neoplastics, and antimicrobials, antihistamines and decongestants.

The drug delivery systems of the present invention are particularly suited for the controlled release of water-insoluble bioactive agents. Examples of water-insoluble active agents include: cannabinoids (like nabilone), steroids, immunosuppressant drugs like cyclosporine, nitroglycerin and serotonin 5-HT3 receptor antagonists like ondansetron.

According to a particularly preferred embodiment, the bioactive agent is selected from the group consisting of cannabinoids. Even more preferably, the bioactive agent is a lipophilic plant derived or synthetic cannabinoid. Most preferably, the bioactive agent is dronabinol (tetrahydrocannabinol; THC).

The present drug delivery systems can advantageously be used for transmucosal delivery of THC, e.g. by buccal or sublingual administration. The drug delivery systems offer the additional advantage that the polyoxazoline-based water-soluble polymer matrix protects THC very effectively against oxidation.

In another preferred embodiment of the present invention, the water-soluble polymer matrix holds 0.1-20%, more preferably 0.3-15% and most preferably 0.5-12% by weight of the polymer matrix of a plasticizer. The use of a plasticizer, besides acting as a plasticizer, offers the additional advantage that it influences the tackiness of the polymer matrix. Thus, plasticizer may be incorporated into the present drug delivery systems to impart excellent muco-adhesive properties.

The plasticizer is preferably homogeneously dispersed throughout the polymer matrix. The plasticizer is not a part of the polymer matrix but is contained in the drug delivery system as part of a discrete phase, e.g. in the delivery vehicle.

In case the present drug delivery system contains a delivery vehicle, it is preferred that both the bioactive agent and the plasticizer are contained in the delivery vehicle. Even more preferably, the delivery vehicle contains at least 50 wt. %, most preferably at least 70 wt. % of the plasticizer. It will be understood that the plasticizer may suitably be employed as the pharmaceutically acceptable solvent for the bioactive agent in accordance with the preferred embodiment described herein before.

The plasticizer is advantageously selected from the group of polyols; esters of polyols and short chain carboxylic acids; and combinations thereof. Examples of polyols that may suitably be employed as free polyol, or in the form of an ester, include glycerol, sorbitol, mannitol, xylitol and combinations thereof. Even more preferably, the polyol or polyol ester is selected from glycerol, glycerol ester, sorbitol, sorbitol ester. Most preferably, the plasticizer is selected from glycerol; esters of glycerol and short chain carboxylic acids; and combinations thereof.

Preferably, the short chain carboxylic acid residues contained in the aforementioned polyol esters are selected from acetic acid, propanoic acid and butanoic acid. Most preferably, the plasticizer is triacetin (1,2,3-triacetoxypropane). Triacetin offers the advantage that it can suitably be used as a solvent for lipophilic bioactive agents.

The inventors have observed that triacetin can be used in the present drug delivery system to produce polymeric films that exhibit strong adhesion to moist skin. When triacetin is incorporated in these films in a concentration of about 1 wt. %, the films as such are non-tacky, but show strong adhesion to wet surfaces, such as mucosa. When triacetin is used in the present drug delivery system in a concentration of around 10% to 30% by weight of the polyoxazoline, it produces a gel at room temperature.

Most preferably, triacetin is employed in the present drug delivery system in a concentration of 0.5-5% by weight of the water-soluble polymer matrix. In accordance with another embodiment, triacetin is employed in the drug delivery system in a concentration of 0.5-8% by weight of the polyoxazoline.

Glycerol and mono-esters of glycerol may suitably be employed as a plasticizer. These plasticizers may simultaneously act as a solvent for hydrophilic bioactive agents. According to another preferred embodiment, the drug delivery system contains 0.5-12 wt. %, even more preferably 1-8 wt. % of glycerol, and a hydrophilic bioactive agent, preferably a hydrolysable, hydrophilic bioactive agent.

Another aspect of the invention relates to method of preparing a drug delivery system as defined herein before, comprising:
 combining a solvent, the polyoxazoline and the bioactive agent to form a solution of the polyoxazoline in the solvent, said solution containing the bioactive agent in dispersed and/or dissolved from; and
 removing the solvent from the solution.

In a particularly preferred embodiment, both the polyoxazoline and the bioactive agent are completely dissolved in the solvent before said solvent is removed.

The present invention also provides an alternative method for the preparation of a drug delivery system as defined herein before, said method comprising:
 combining the bioactive agent and the polyoxazoline to form a mixture having a temperature above the glass transition temperature of said mixture;

cooling the mixture to a temperature below said glass transition temperature.

In accordance with a particularly preferred embodiment the mixture comprising the bioactive agent and the polyoxazoline is cooled at a sufficiently high rate to solidify both the bioactive agent and the polyoxazoline in an amorphous state. Any liquid can be made into an amorphous solid by employing a sufficiently high cooling rate (melting method). If the cooling rate is faster than the rate at which molecules can organize into a more thermodynamically favorable crystalline state, then an amorphous solid will be formed. Because of entropy considerations (e.g. low crystallization energy), many polymers can be made amorphous solids by cooling even at slow rates.

The plasticizers mentioned herein before are advantageously incorporated in the mixture comprising the bioactive agent and the polyoxazoline as these reduce the glass transition temperature of the polyoxazoline. Thus, thermal degradation of bioactive agents can be minimized. The combining of the bioactive agent and the polyoxazoline to form a mixture having a temperature above the glass transition temperature of said mixture and the subsequent cooling to produce, for instance, a solid solution of the bioactive agent in the polyoxazoline may suitably be achieved any one of the following techniques:

hot spin melting;
hot melt granulation;
melt filling of capsule
microwave (US 2006/051422)
melt extrusion/injection molding In order to remove traces of monomers, organic solvent residues or other impurities, it can be advantageous to subject the polyoxazoline, the present drug delivery device or an intermediate of the present drug delivery device to solvent extraction. Extraction with a supercritical or near critical fluid, or a liquefied gas is particularly preferred as these solvents can easily be removed quantitatively. Carbon dioxide is particularly suitable solvent.

The invention is further illustrated by means of the following non-limiting examples.

EXAMPLES

Example 1

Three different film formulations with THC ($\Delta^9$-tetrahydrocannabinol) were prepared to be challenged with pure oxygen for 7 days at 40° C. for comparison of stability data.
[1] The first film (Film 1) was prepared according to WO 02/064109 A2 (GW Pharma Ltd), example 2 with 1.5% (w/w) THC based on the dried formulation;
[2] The second film (Film 2) was prepared by dissolving gelatin (1 g), propylene glycol alginate (0.1 g), polyvinyl alcohol (0.1 g) and glycerol (0.75 mL) in hot water (10 mL). A 2.5-mL solution of 0.05 g THC in ethanol with 0.17 g Pluronic® 127 was added and the mixture was dried in an oven at 40° C. under vacuum (end concentration THC in dried film was 1.0%);
[3] The third film (Film 3) was prepared without the use of water by dissolving Aquazol® 200 (2 g), triacetin (0.1 mL) and 0.05 g THC in 10 mL ethanol. Aquazol® 200 is a poly(2-oxazoline) that is marketed by International Specialty Products Inc. The clear solution was casted in a Teflon® dish and dried in an oven at 40° C. under vacuum (end concentration THC in dried film was about 2.5%).

All three formulations were subjected to pure oxygen stress for 7 days at 40° C. in the dark. The formulations were tested in the form of a film and in the form of a grinded film. Grinded films were prepared by milling the films in liquid nitrogen to powder.

Before and after the stress test films were extracted with ethanol and the extracts were analyzed on HPLC to determine the total cannabinoids concentration, the THC concentration and the concentration of CBN (cannabinol). As the main oxidation product from THC is CBN, the latter can suitably be used to assess a film's capability of protecting THC against oxidation. Also increases in concentrations of other non-THC cannabinoids are indicative of THC degradation.

The results from the HPLC analyses are depicted in Table 1:

TABLE 1

(concentrations in parts by weight)

| | Film 1 | Film 2 | Film 3 |
|---|---|---|---|
| Freshly prepared | | | |
| THC | 99.1 | 99.4 | 99.3 |
| CBN | 0.15 | 0.14 | 0.14 |
| Other cannabinoids | 0.73 | 0.47 | 0.54 |
| Film after stress | | | |
| THC | 98.8 | 79.2 | 98.9 |
| CBN | 0.30 | 1.84 | 0.15 |
| Other cannabinoids | 0.95 | 5.47 | 0.92 |
| Unidentified decomposition products | | 13.2 | |
| Grinded film after stress | | | |
| THC | 98.8 | 91.0 | 99.2 |
| CBN | 0.27 | 0.91 | 0.16 |
| Other cannabinoids | 0.94 | 2.07 | 0.65 |
| Unidentified decomposition products | | 5.4 | |

It is clear from these results that the formulations based on the poly(2-oxazoline) Aquazol® (Film 3) had the highest stability, even though the THC payload (2.5 wt. %) of these formulations was substantially higher than that of the other formulations (1.0 wt. % and 1.5 wt. %).

Surprisingly, the data show that grinded films were more stable than the non-grinded films in this oxygen stress experiment. A possible explanation lies in the very low water content of the oxygen used (not more than 67 ppm), which may have resulted in more effective drying of grinded films than of the non-grinded films. It seems the water content in the final formulation is crucial for the stability of THC: the less water, the better the stability of THC.

Example 2

A film 2A was prepared using the same formulation and procedure as for film 3 of Example 1. In addition, a film 2B was produced that was identical to film A, except that triacetin was replaced by glycerol. Finally, a film 2C was produced that was identical to films 2A and 2B, except that it did not contain a plasticizer.

Films 2A, 2B and 2C were subjected to dissolution tests in conformity with the United States Pharmacopoeia standard basket method at 100 RPM. The dissolution medium consisted of 500 mL 1% g/v sodium lauryl sulphate and 5 film samples containing 2.5 mg THC each were tested together in one basket in order to reach high enough concentrations in the dissolution medium to assess the dissolution rate via online UV-measurements. The results so obtained are shown in Table 2.

TABLE 2

| (percentage THC dissolved) | | | |
|---|---|---|---|
| | Film 2A | Film 2B | Film 2C |
| After 1 minute | 22 | 21 | 11 |
| After 2 minutes | 72 | 58 | 50 |
| After 5 minutes | 100 | 99 | 91 |

Example 3

Films 3A-3C were prepared using the same formulation and procedure as for film 3 of Example 1, except that the THC loading was increased to 10% (Film 3A), 15% (Film 3B) and 20% (Film 3C). The films were subjected to 3 months storage at 40° C. in the dark. The formulations were tested in the form of a film at ambient humidity. The results are depicted in Table 3.

TABLE 3

| (concentrations in parts by weight) | | | |
|---|---|---|---|
| 40° C. (ambient relative humidity) | Film 3A | Film 3B | Film 3C |
| Freshly prepared | | | |
| THC | 98.9 | 98.8 | 98.9 |
| CBN | 1.13 | 1.15 | 1.11 |
| Other cannabinoids | n.d. | n.d. | n.d. |
| Film after 3 months | | | |
| THC | 98.2 | 98.6 | 97.2 |
| CBN | 1.77 | 1.38 | 2.80 |
| Other cannabinoids | n.d. | n.d. | n.d. |

*: n.d.: not detected

Example 4

Grinded films 4A-4E were prepared using the same procedure as for film 3 of Example 1, except that Plasdone® K90 (Film 4A), Soluplus® (Film 4B), Eudragit® 100 cationic copolymer (Film 4C), Aquazol-200® (Film 4D) and Aquazol-500® (Film 4E) were used to formulate. The grinded films were subjected to the same accelerated storage test as described in Example 1 with the addition that samples were shaken once a day to obtain maximum penetration of oxygen and that oxygen was refreshed on a daily basis. The results are depicted in Table 4.

TABLE 4

| (concentrations in parts by weight) | | | | | |
|---|---|---|---|---|---|
| 40° C. (100% oxygen) | Film 4A | Film 4B | Film 4C | Film 4D | Film 4E |
| Freshly prepared | | | | | |
| THC | 98.8 | 99.0 | 98.9 | 98.8 | 98.8 |
| %-impurities (mostly CBN) | 1.2 | 1.0 | 1.1 | 1.2 | 1.2 |
| Grinded film after 1 week | | | | | |
| THC | 51.9 | 74.2 | 80.2 | 90.1 | 94.3 |
| %-impurities (mostly CBN) | 48.1 | 25.8 | 19.8 | 9.90 | 5.73 |

The results show that solid dispersions prepared with Aquazol-200® and Aquazol-500® had superior oxygen barrier properties compared to other solid dispersions of THC.

Stability and dissolution test results as presented in examples 1 through 4 are markedly better compared to those described in PCT/US2005/044375, PCT/EP03/50087 and US2006/0257463.

Example 5

Different film formulations with indometacin and fluconazol were prepared. Indometacin films were prepared by dissolving Aquazol® 200 or Aquazol® 500, triacetin (1 to 10%) and indometacin (10 to 50%) in ethanol. Fluconazol films were prepared by dissolving Aquazol® 200 or Aquazol® 500, glycerol (1 to 10%) and fluconazol (10 to 50%) in ethanol. The clear solutions were casted in a Teflon® dish and dried in an oven at 40° C. under vacuum (end concentration of the active pharmaceutical ingredients (API's) in the films ranged between 10 to 50%, w/w).

The clear transparent film samples were clamped within a powder pocket held in a single cantilever bend geometry. Loading masses for films were 20 to 25 mg and for powders (the API as a reference) approximately 10 mg. An oscillating stress was applied and resultant strain measured. Displacement 0.05 mm, oscillation frequencies 1, 10 & 30 Hz. Samples were heated at 2° C./min from ambient to 180° C. Aim of this procedure is to measure the glass transition or melting behavior (DMA analysis) within the sample films.

If a composite sample is in an amorphous state, it will undergo a glass transition corresponding to a decrease in heat capacity. A downward shift will be observed in the plot, and this endothermic transition is used to determine the composite's $T_g$.

Frequently, the glass transition is accompanied by an enthalpy relaxation, which is seen as an endothermic signal superimposed on the glass transition. The existence of a single phase may be indicated by several criteria such as, for example, optical clarity, a single glass transition temperature and scattering methods.

For all samples a single glass transition was observed. The temperature of this transition increased with the molecular weight of the Aquazol. The DMA results indicate that films with indometacin loads up to 50% and fluconazol loads up to 35% are a solid solution, as no melting transition was seen and a single $T_g$ was observed.

Example 6

A fluconazol film was prepared by dissolving Aquazol® 200 (35 wt. %), glycerol (30 wt. %) and fluconazol (35 wt. %) in ethanol. The clear solution so obtained was casted and dried in the same way as in Example 5. The fluconazal contained in this film showed a stronger tendency to crystallize than the fluconazal contained in similar films containing less glycerol (Example 5).

Example 7

Indometacin films were prepared by dissolving indometacin with equal amounts of, respectively, Aquazol® 200 (Film 6A), Aquazol® 500 (Film 6B) and Soluplus® (Film 6C) in ethanol. The clear solutions were casted in a Teflon® dish and dried in an oven at 40° C. under vacuum (end concentration indometacin in the clear transparent yellow films was 50%, w/w). The remaining ethanol residue was 800 ppm or less, well below the limit of 5000 ppm as per pharmacopoeial guidance.

A fourth Aquazol® 200 film (Film 6D) was prepared the same way with incorporation of 20% w/w Calofort® SV, nano calcium carbonate (CaCO$_3$), suspended, having a weight averaged diameter within the range of 50-300 nm just before casting. The Films 6A, 6B, 6C and 6D were subjected to dissolution tests in conformity with the United States Pharmacopoeia standard basket method at 100 RPM. The dissolution media consisted of phosphate buffer pH 7.2 (Buffer A), acetate buffer pH 4.5 (Buffer B) and sodium chloride/hydrochloric acid pH 1.2 buffer (Buffer C), all in conformity with European Pharmacopoeia Chapter 2.9.3. The indometacin dissolution rate was analysed with UV at 320 nm.

The results so obtained are shown in Table 5a, 5b and 5c.

TABLE 5a (percentage indometacin dissolved)

| Buffer A - pH 7.2 | Film 6A | Film 6B | Film 6C | Film 6D |
|---|---|---|---|---|
| After 5 minutes | 10.2 | 8.6 | 7.9 | 25.6 |
| After 15 minutes | 29.9 | 24.5 | 18.7 | 50.1 |
| After 60 minutes | 70.8 | 64.9 | 62.3 | 81.7 |
| After 120 minutes | 79.8 | 81.7 | 84.5 | 92.9 |
| After 1320 minutes | 100.0 | 100.0 | 100.0 | 100.0 |

TABLE 5b (percentage indometacin dissolved)

| Buffer B - pH 4.5 | Film 6A | Film 6B | Film 6C | Film 6D |
|---|---|---|---|---|
| After 5 minutes | 0.5 | 2.9 | 3.3 | 13.6 |
| After 15 minutes | 1.1 | 3.1 | 2.6 | 21.3 |
| After 60 minutes | 3.5 | 4.3 | 3.5 | 45.9 |
| After 120 minutes | 6.1 | 6.5 | 3.9 | 57.1 |
| After 1080 minutes | 37.2 | 39.0 | 10.3 | 78.9 |

TABLE 5c (percentage indometacin dissolved)

| Buffer C - pH 1.2 | Film 6A | Film 6B | Film 6C | Film 6D |
|---|---|---|---|---|
| After 5 minutes | 0.1 | 0.1 | 0.8 | 0.1 |
| After 15 minutes | 0.2 | 0.2 | 1.4 | 0.1 |
| After 60 minutes | 0.4 | 0.5 | 2.9 | 0.2 |
| After 120 minutes | 0.7 | 0.8 | 4.3 | 0.4 |
| After 1320 minutes | 5.8 | 6.5 | 21 | 3.4 |

Example 8

The effect of exposure to gastric fluid on polyoxalines of different molecular weights was investigated. Ten gram samples of poly-ethyl-oxazolines (Aquazol®) with Mw 5,000; 50,000; 200,000 and 500,000 were dissolved in 500 mL Simulated Gastric Fluid (at pH 1.0) and 500 mL Simulated Intestinal Fluid (at pH 6.8) respectively.

The mixtures were incubated at 37° C. while gently shaken. After 6 hours samples were taken. Samples (1.5 mL) were acidified with 5 drops of hydrochloric acid (1N) and 0.5 grams sodium chloride. As soon as possible after sampling and sample preparation, the 1.5 mL aliquots were extracted with diethyl ether (1.5 mL). The diethyl ether top layer was subjected to GC analysis to assess the formation of propionic acid that is a direct indicator for the formation of PEtOx-polyethyleneimine (PEI) copolymer-derivative(s). The sample preparation and subsequent GC-analytical procedure was validated for its intended purpose: linearity, reproducibility, lower limit of quantification (LLOQ) and recoveries were determined and found to comply with ICH-Guidance. GC settings were as follows: injector temperature 225° C., detector temperature 250° C., split liner (split: 1:10), flow: 1.8 ml/min, temperature program: 125° C. hold 5 min; 125° C. to 180° C. in 3.66 minutes and 180° C. hold 12 minutes. Supelcowax® column 10, 30 m×0.32 mm with film thickness 0.25 µm.

Decomposition in m/m % was calculated from the amount of propionic acid formed during the decomposition test. As an example: 10 mg propionic acid corresponds to 99/57× 10=17.4 mg of decomposed poly(2-oxazoline) (Mw of propionic acid is 57; Mw of one polyethyloxazoline building block is 99). In case 10 mg of propionic acid is found in a sample that originally contained 20 grams of poly(2-oxazoline), the m/m(%) decomposition is calculated as [17.4/1000]/20×100%=0.09%. The obtained results are depicted in Table 6

TABLE 6

(Decomposition in m/m %)

| Molecular weight | pH 1.0 (SGF) - after 6 hours | pH 6.8 (SIF) - after 6 hours |
|---|---|---|
| 5,000 g/mole | 0.53 | 0.13 |
| 50,000 g/mole | 0.40 | 0.07 |
| 200,000 g/mole | 0.14 | 0.02 |
| 500,000 g/mole | 0.08 | 0.01 |

The invention claimed is:

1. A drug delivery system comprising a solid dispersion of an amorphous cannabinoid in a water-soluble polymer matrix, said water-soluble polymer matrix comprising at least 50 wt. % of polyoxazoline having a molar mass of at least 40,000 g/mol and said cannabinoid being contained in the solid dispersion in a concentration of at least 0.5% by weight of the water-soluble polymer matrix.

2. The drug delivery system according to claim 1, wherein the solid dispersion is a solid solution.

3. The drug delivery system according to claim 2, wherein the solid solution has a glass transition temperature ($T_g$) of at least 45° C.

4. The drug delivery system according to claim 2, wherein the cannabinoid has a $T_g$ of less than 40° C.

5. The drug delivery system according to claim 4, wherein the cannabinoid has a $T_g$ of −30° C. to less than 40° C. and wherein said cannabinoid is contained in the drug delivery system in a concentration of 0.5-30% by weight of the water-soluble polymer matrix.

6. The drug delivery system according to claim 1, wherein the amorphous cannabinoid in the form of nanoparticles having a volume weighted average diameter of less than 100 nm.

7. The drug delivery system according to claim 1, wherein the polyoxazoline has a molar mass of at least 80,000 g/mol.

8. The drug delivery system according to claim 7, wherein the polyoxazoline has a molar mass of at least 150,000 g/mol.

9. The drug delivery system according to claim 1, wherein the polyoxazoline is a poly(N-acylalkylenimine) having repeating units comprising the formula $(CH_2)_m NCOR^1$; $R^1$ being selected from H, $C_{1-22}$ alkyl, cycloalkyl, aralkyl, aryl; and m being 2 or 3.

10. The drug delivery system according to claim 1, wherein the water-soluble polymer matrix represents 20-99.999 wt. % of the drug delivery system.

11. The drug delivery system according to claim 1, wherein the drug delivery system is in the form of a powder, a tablet, a capsule or a mucoadhesive sheet.

12. The drug delivery system according to claim 1, wherein the drug delivery system is a powder having a mass weighted average diameter of 0.1-250 μm.

13. The drug delivery system according to claim 1, wherein the drug delivery system comprises a powder having a mass weighted average diameter of 0.1-250 μm in the form of an oral dosage unit selected from a tablet and a capsule.

14. The drug delivery system according to claim 1, wherein the drug delivery system is a mucoadhesive sheet comprising at least 20 wt. % of a water-soluble polymer matrix in the form of thin film.

15. A method of preparing a drug delivery system according to claim 1, comprising:
   (a) combining a solvent, the polyoxazoline and the cannabinoid to form a solution of the polyoxazoline in the solvent, said solution comprising the cannabinoid in dispersed and/or dissolved from; and
   (b) removing the solvent from the solution.

16. A method of preparing a drug delivery system according to claim 1, comprising:
   (a) combining the cannabinoid and the polyoxazoline to form a mixture having a temperature above the glass transition temperature of said mixture; and
   (b) cooling the mixture to a temperature below said glass transition temperature.

\* \* \* \* \*